United States Patent [19]

Tai

[11] Patent Number: 5,013,557

[45] Date of Patent: May 7, 1991

[54] TASTE MASKING COMPOSITIONS COMPRISING SPRAY DRIED MICROCAPSULES CONTAINING SUCRALFATE AND METHODS FOR PREPARING SAME

[75] Inventor: Anna W. Tai, Bridgewater, N.J.

[73] Assignee: Warner-Lambert Company, Morris Plains, N.J.

[21] Appl. No.: 416,630

[22] Filed: Oct. 3, 1989

[51] Int. Cl.$^5$ ............................................. A61K 9/58
[52] U.S. Cl. ................................... 424/493; 424/439; 424/498; 424/499; 424/500; 424/501; 427/3
[58] Field of Search ............. 424/501, 493, 499, 498, 424/500, 489, 78, 439, 440, 442; 427/3

[56] References Cited

U.S. PATENT DOCUMENTS

| | | | |
|---|---|---|---|
| 3,663,253 | 5/1972 | Stone | 424/195.1 X |
| 4,271,142 | 6/1981 | Puglia et al. | 424/440 |
| 4,615,697 | 10/1986 | Robinson | 424/78 X |
| 4,704,278 | 11/1987 | Wu | 424/688 |
| 4,716,041 | 12/1987 | Kjornaes et al. | 424/468 |
| 4,824,675 | 4/1989 | Wong et al. | 424/468 |
| 4,910,023 | 3/1990 | Botzolakis | 424/470 |

Primary Examiner—Thurman K. Page
Attorney, Agent, or Firm—Charles A. Gaglia, Jr.

[57] ABSTRACT

The present invention pertains to spray dried spheroidal microcapsules under about 150 microns in diameter which comprise in percentages by weight of the microcapsule composition (a) sucralfate present in an amount from about 1% to about 70%, and (b) a polymer soluble in the gastric fluids present in an amount from about 30% to about 99%. In another embodiment, the invention is directed at a taste masking composition which comprises a therapeutically effective amount of a spray dried spheroidal microcapsule core under about 150 microns in diameter and a matrix over the core wherein the taste masking composition comprises (A) a microcapsule core comprising in percentages by weight of the core composition (a) sucralfate present in an amount from about 1% to about 70%, and (b) a polymer soluble in the gastric fluids present in an amount from about 30% to about 99%; and (B) a matrix over the core comprising in percentages by weight of the matrix composition (a) a bulking agent present in an amount up to about 99.9%, and (b) a lubricating agent present in an amount from about 0.1% to about 7%.

47 Claims, 1 Drawing Sheet

TASTE MASKING COMPOSITIONS COMPRISING SPRAY DRIED MICROCAPSULES CONTAINING SUCRALFATE AND METHODS FOR PREPARING SAME

BACKGROUND OF THE INVENTION

1. Field of the Invention

This invention pertains to novel medicated compositions useful in treating ulcers. More particularly, this invention pertains to novel chewable spray dried spheroidal microcapsules and taste masking compositions. The novel microcapsule compositions comprise sucralfate and a polymer soluble in the gastric fluids. In one embodiment, therapeutically effective amounts of the sucralfate microcapsules may be incorporated into a matrix comprising a bulking agent and a lubricating agent and compressed into tablets to prepare taste masking compositions. In another embodiment, therapeutically effective amounts of the sucralfate microcapsules may be utilized in a wide variety of pharmaceutically acceptable carriers and confectionery bulking agents to prepare medicated products having taste masking properties. This invention also relates to methods for preparing these chewable spray dried spheroidal microcapsules and the medicated taste masking compositions in which they may be used.

2. Description of the Prior Art

Peptic ulcers are lesions in the mucous membrane of the esophagus, stomach or duodenum caused by gastric acid and pepsin. Peptic ulcers are believed to be caused by hypersecretion of gastric fluids or decreased resistance of the mucous membrane to the action of gastric acids and pepsin.

The methods for treating ulcers include diet modification, surgical removal of the ulcer, and the use of drugs. Useful antiulcer drugs include antacids, which neutralize excess acid secretion; anticholinergics, which diminish acid secretion; histamine $H_2$ receptor blocking agents, which block gastric acid secretion; prostaglandins, which increase mucous membrane resistance to gastric fluids; prokinetic agents, which enhance gastrointestinal motility; and gel forming compositions, which form ulcer protective barriers.

A gel forming drug in this last category is sucralfate, which is well known in the art as a basic aluminum sucrose sulfate complex which accelerates the healing of peptic ulcers. The mechanism by which sucralfate works is not fully understood but it is known that the sulfated disaccharide is not absorbed from the gastrointestinal tract and that the antiulcer activity is therefore exerted locally and not systemically. Sucralfate has a greater affinity for ulcerated mucosa than for nonulcerated mucosa and produces morphological and functional changes in the mucosa. These changes include mucus release, changes in ion transport and increased release and synthesis of prostaglandins (i.e., prostaglandin $E_2$) from the mucosa.

At pH values below about 3.5, sucralfate coagulates to form a gel-like mass. In the gastrointestinal tract, this gel-like mass concentrates at ulcer sites to produce an ulcer adherent cytoprotective barrier with proteinaceous exudate. This protein barrier (a) binds to the ulcer site to form a protective barrier which blocks diffusion of hydrogen ions, (b) adsorbs bile salts and inhibits the potential ulcerogenic properties of pepsin, and (c) blocks back diffusion of gastric acid across the sucralfate protein barrier. The antiulcer effects of sucralfate are not attributed to neutralization of gastric acid because sucralfate has negligible acid-neutralizing capability.

The relatively large dosage level of sucralfate of one (1) gram four times daily presents certain drawbacks in administering sucralfate antiulcer therapy. Non-chewable tablets or capsules are physically very large and may be objectionable to certain consumers. Hard chewable tablets offer the ability to deliver large dosages of sucralfate, however, the resulting products have a gritty mouth feel and are dominated by the astringent taste of sucralfate.

U.S. Pat. No. 4,772,470, issued to Inoue et al. and assigned to Nitto Electric Industrial Co., Ltd., discloses an oral bandage comprising a film support for a soft adhesive film comprised of a mixture of a polycarboxylic acid and/or a polycarboxylic acid anhydride and a vinyl acetate polymer. The oral bandage may have incorporated therein a topical drug such as sucralfate for administration to the oral mucosa.

U.S. Pat. No. 4,704,278, issued to Wu et al. and assigned to American Home Products Corp., discloses an aqueous antacid composition of fluidized magaldrate suspension comprising magaldrate gel (aluminum hydroxide and magnesium hydroxide) and a fluidizing amount of a combination of an aluminum hydroxide gel as a first fluidizer and a pharmaceutically acceptable citric ion source as a second fluidizer. The composition may also contain other therapeutically active substances such as sucralfate.

U.S. Pat. No. 4,676,984, also issued to Wu et al. and assigned to American Home Products Corp., discloses an aqueous antacid composition of fluidized magaldrate suspension comprising magaldrate gel and a fluidizing amount of a combination of an aluminum hydroxide gel as a first fluidizer and a pharmaceutically acceptable citric ion source as a second fluidizer, and a polyhydric alcohol. The composition may also contain other therapeutically active substances such as sucralfate.

U.S. Pat. Nos. 4,670,185 and 4,676,984, issued to Fujiwara et al. and assigned to Lion Corporation, discloses an aqueous vesicle dispersion comprising (1) a nonionic surfactant selected from polyethylene castor oil ethers and polyethylene hydrogenated castor oil ethers, (2) a nonionic surfactant which is a sorbitan polyester, and (3) an ionic surfactant. The dispersions may be used as release-controlled agents and may contain topical agents such as peptic ulcer remedy medicaments which include sucralfate.

U.S. Pat. No. 4,615,697, issued to Robinson and assigned to Bio-Mimetics, Inc., discloses a controlled release composition comprising a bioadhesive comprised of a water-swellable but water-insoluble carboxy-functional polymer and a treating agent which may be sucralfate.

M. Itch et al., Gastroenterology, 96, p. A229 (May 1989), "Combination of EGF and Sucralfate Significantly Accelerates The Healing of Chronic Gastric Ulcers In The Rat," discloses the combination of epidermal growth factor (EGF) and sucralfate for treatment of chronic gastric ulcers. Sucralfate is said to enable EGF to remain in the stomach at a high concentration.

A frequently encountered problem in the field of chewable medicament encapsulated compositions is unsuitable particle size and shape. Particle sizes larger than about 850 microns are usually considered unsatisfactory for chewing because these particles are gritty and are easily broken during chewing thereby causing premature release of the medicament in the mouth with an accompanying off-taste. Spheroidal particles are generally preferred over non-spheroidal particles because these uniformly coated materials protect the medicament from premature release and release the medicament more uniformly.

Small medicament encapsulated particles, or microcapsules, suitable for use in chewing compositions are generally easier to prepare with a solvent-based film coating because of the high volatility and low surface tension of the solvent. For the reasons set out above, microcapsules prepared from aqueous-based coating materials are usually preferred, however, these microcapsules are generally larger in size than those obtained from solvent-based coating materials and must be ground to obtain smaller chewable microcapsules. These ground smaller particles are usually not satisfactory for use in medicament encapsulated compositions because the particles are irregular, are not spheroidal and do not release the medicament uniformly.

U.S. Pat. No. 4,749,575, issued to Rotman and assigned to Bio-Dar Ltd., discloses the preparation of chewable microcapsules of less than 300 microns diameter formed by dissolving a polymer such as hydroxypropyl methylcellulose phthalate, hydroxyphenyl methylcellulose or various acrylic resins in an organic solvent and coating a medicament with the polymer solution in a fluidized bed.

European patent application no. 266,113 discloses a method for preparing a taste masked therapeutic composition which comprises spray drying a suspension of acetoaminophen in a solution of an acrylic polymer in an organic solvent.

European patent application no. 250,648 and Goodman et al., *Journal of Pharmaceutical Sciences*, 59, 1131-1137 (1970), disclose methods for preparing microspheres suitable for formulating into a tablet which comprise slurrying an aqueous mixture of a drug and an acrylic polymer, vacuum drying the mixture, then grinding the so-formed particles, and compressing the particles into a tablet.

PCT application no. PCT/U.S.87/03068 discloses a method for preparing a taste-masked pharmaceutical composition which comprises spraying in a fluidized bed a suspension comprised of a mixture of an aqueous based solution of a high temperature film forming polymer and a low temperature film forming polymer onto particles of a pharmaceutical core material. The high temperature film forming polymer can be ethyl cellulose or an acrylic polymer and the low temperature film forming polymer can be an acrylic polymer.

European patent application no. 265,226 discloses a method for preparing a taste masked therapeutic composition which comprises spray drying a suspension of colloidal silica in an alcoholic solution of acetoaminophen and ethyl cellulose.

U.S. Pat. No. 4,764,380, issued to Urquhart et al. and assigned to Alza Corporation, discloses a drug delivery system for microcapsules which can be prepared from an aqueous mixture of the drug and ethyl cellulose. The mixture is blended and kneaded, then extruded and passed through a 20 mesh screen. The microcapsules may be coated with ethyl cellulose by air suspension.

While the above medicament encapsulated compositions provide some degree of taste masking activity, none of the above compositions are entirely satisfactory. Chewable encapsulated compositions prepared from organic solvent based polymer solutions are expensive and pose environmental and toxicity problems. Chewable encapsulated compositions prepared from aqueous dispersions of polymers generally provide large microcapsules which must be ground to smaller particles which are usually not uniform in size, shape and composition. Thus it would be advantageous to prepare an encapsulated composition from an aqueous dispersion of polymer whereby the microcapsules formed are spheroidal and are of sufficiently small size such that they are not gritty and can be chewed without being broken. The present invention provides such improved chewable spheroidal microcapsules and taste masking compositions without the disadvantages characteristic of previously known products. The present invention also provides methods for preparing these improved spheroidal microcapsules and taste masking compositions in which they may be employed.

SUMMARY OF THE INVENTION

The present invention pertains to spray dried spheroidal microcapsules under about 150 microns in diameter which comprise in percentages by weight of the microcapsule composition (a) sucralfate present in an amount from about 1% to about 70%, and (b) a polymer soluble in the gastric fluids present in an amount from about 30% to about 99%. In another embodiment, the invention is directed at a taste masking composition which comprises a therapeutically effective amount of a spray dried spheroidal microcapsule core under about 150 microns in diameter and a matrix over the core wherein the taste masking composition comprises (A) a microcapsule core comprising in percentages by weight of the core composition (a) sucralfate present in an amount from about 1% to about 70%, and (b) a polymer soluble in the gastric fluids present in an amount from about 30% to about 99%; and (B) a matrix over the core comprising in percentages by weight of the matrix composition (a) a bulking agent present in an amount up to about 99.9%, and (b) a lubricating agent present in an amount from about 0.1% to about 7%. Therapeutically effective amounts of the microcapsule compositions may be utilized in a wide variety of pharmaceutically acceptable carriers and confectionery bulking agents to prepare medicated products having taste masking properties. This invention also relates to methods for preparing these microcapsules and the taste masking compositions in which they may be employed.

DETAILED DESCRIPTION OF THE INVENTION

Figure 1:
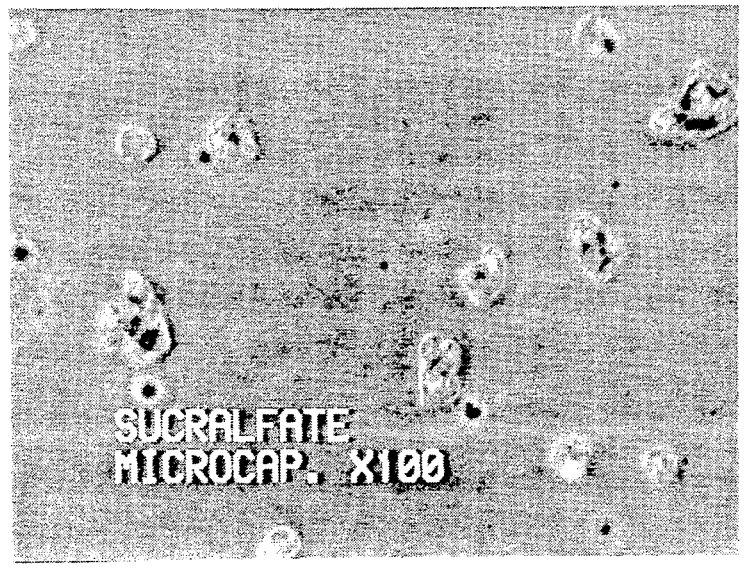
FIG. 1 is a picture of spray dried spheroidal microcapsules of sucralfate and maltodextrin (magnification 100X, Example 1). The spheroidal appearance is clearly seen.

The present invention pertains to improved chewable spray dried spheroidal microcapsules and taste masking compositions for administering a medicament such as sucralfate. More specifically, the present invention pertains to spray dried spheroidal microcapsules under about 150 microns in diameter which comprise in percentages by weight of the microcapsule composition (a) sucralfate present in an amount from about 1% to about 70%, and (b) a polymer soluble in the gastric fluids present in an amount from about 30% to about 99%.

In another embodiment, the invention is directed at a taste masking composition which comprises a therapeutically effective amount of a spray dried spheroidal microcapsule core under about 150 microns in diameter and a matrix over the core wherein the taste masking composition comprises (A) a microcapsule core comprising in percentages by weight of the core composition (a) sucralfate present in an amount from about 1% to about 70%, and (b) a polymer soluble in the gastric fluids present in an amount from about 30% to about 99%, and (B) a matrix over the core comprising in percentages by weight of the matrix composition (a) a bulking agent present in an amount up to about 99.9%, and (b) a lubricating agent present in an amount from about 0.1% to about 7%.

Therapeutically effective amounts of the microcapsule compositions may be utilized in a wide variety of pharmaceutically acceptable carriers and confectionery bulking agents to prepare medicated products having taste masking properties. This invention also relates to methods for preparing these microcapsules and the taste masking compositions in which they may be employed.

While the invention is not to be limited to theoretical considerations, applicant believes that by carefully controlling the concentration of sucralfate and a polymer soluble in the gastric fluids in an aqueous suspension, and carefully controlling the conditions of spray drying the suspension, spheroidal microcapsules of sufficiently small particle size suitable for use in chewable medicated compositions can be prepared. By forming the microcapsules by spray drying, applicant's microcapsules are spheroidal and mask the taste of sucralfate more uniformly than prior art compositions. Moreover because applicant's microcapsule compositions are prepared from aqueous slurries, the resulting compositions are more economical to prepare and do not have the potential toxicity and environmental problems which can accompany the preparation of such compositions from organic solutions. While the inventive microcapsules have good taste masking properties, improve the mouth feel and overall chew characteristics of the medicament and improve the compressibility of sucralfate, these properties can be enhanced by incorporating the medicament into a pharmaceutically acceptable carrier or confectionery bulking agent such as tablet. By carefully controlling the conditions for compressing the spheroidal microcapsules into tablets, taste masking compositions can be prepared suitable for use in chewable medicated compositions.

In a preferred embodiment, the spray dried spheroidal microcapsules comprise in percentages by weight of the microcapsule composition (a) sucralfate present in an amount from about 1% to about 70%, and (b) a polymer soluble in the gastric fluids present in an amount from about 30% to about 99%. In a more preferred embodiment, the spray dried spheroidal microcapsules comprise in percentages by weight of the microcapsule composition (a) sucralfate present in an amount from about 1% to about 60%, and (b) a polymer soluble in the gastric fluids present in an amount from about 40% to about 99%. In a most preferred embodiment, the spray dried spheroidal microcapsules comprise in percentages by weight of the microcapsule composition (a) sucralfate present in an amount from about 1% to about 50%, and (b) a polymer soluble in the gastric fluids present in an amount from about 50% to about 99%.

In an alternative embodiment, the spray dried spheroidal microcapsules may further comprise a plasticizing agent present in an amount from about 5% to about 30%, preferably in an amount from about 5% to about 24%, and more preferably in an amount from about 5% to about 20%, by weight of the microcapsule composition.

As set out above, sucralfate, also known as alpha-D-glucopyranoside, beta-D-fructofuranosyl-, octakis-(hydrogen sulfate), aluminum complex, is a basic aluminum sucrose sulfate complex which accelerates the healing of peptic ulcers. Sucralfate is a white amorphous powder which is soluble in dilute acid and base but is practically insoluble in water. At pH values below about 3.5, sucralfate coagulates to form a gel-like mass. Sucralfate is commercially available under the tradename CARAFATE, which is distributed by Marion Laboratories, Kansas City, Mo.

The dosage of sucralfate employed in the present invention is the therapeutically effective dosage required to obtain the desired result. Such dosages are known to the skilled practitioner in the medical arts and are not a part of the present invention. In general, the recommended dosage is one (1) gram of sucralfate four (4) times daily.

The polymers soluble in the gastric fluids useful in the present invention are those polymers which will bind to sucralfate to form spray dried spheroidal microcapsule with taste masking properties and will dissolve in the gastric fluids to permit sucralfate to form a cytoprotective gel. In general, these polymers are water-soluble polymers but may also include those polymers which are not water-soluble at neutral pH values but which are soluble in the gastric fluids at acidic pH values. Polymers which will not release sucralfate in the gastric fluids are not useful in the present invention. Suitable polymers soluble in the gastric fluids in the present invention may be selected from the group consisting of maltodextrins, gelatin, acacia, agar, alginic acid, carrageenan, guar, pectin, tragacanth, xanthan, carboxymethyl cellulose, methyl cellulose, microcrystalline cellulose, polyacrylic acid, polyvinyl alcohol, polyvinyl pyrrolidone polymers, and the like, and mixtures thereof. In a preferred embodiment, the polymer soluble in the gastric fluids is selected from the group consisting of maltodextrins, gelatin, alginic acid, and mixtures thereof. In a most preferred embodiment, the polymer soluble in the gastric fluids is maltodextrin.

Maltodextrins are nonsweet, nutritive saccharide polymers which consist of D-glucose units linked primarily by alpha-1,4 bonds having a dextrose equivalence [DE] of less than 20. Maltodextrins can act as binding agents and diluents in direct compression tablet formulations and provide compressibility and flowability. Maltodextrins are white powders composed of water-soluble glucose polymers obtained by the reaction of corn starch with acid and/or enzymes in the presence of water. Dextrose equivalence is a measure of the degree of starch polymer hydrolysis determined by quantitative analysis. Dextrose equivalence is defined as the amount of reducing sugars expressed as dextrose and reported as a percentage of the dry substance. A particularly preferred maltodextrin is distributed under the tradename MALTRIN, which is manufactured by Grain Processing Corporation, Muscatine, Iowa.

Plasticizing agents (plasticizers) are organic molecules added to a polymer to facilitate processing and to increase the flexibility and toughness of the final product by internally modifying (solvating) the polymer molecule. Plasticizing agents should be soluble in the polymer they are designed to plasticize, should be water-soluble, and should be safe for the intended use. Suitable plasticizing agents in the present invention are nonvolatile organic liquids and low melting solids, such as esters of phthalic acid, adipic acid and sebacic acid, and polyols such as ethylene glycol, propylene glycols, and their derivatives, tricresyl phosphate, castor oil, and the like, and mixtures thereof. Other suitable partly water-soluble to water-insoluble plasticizing agents that may be incorporated include triethyl citrate, tributyl citrate, triacetin, and acetylated mono-, di- and triglycerides, and the like, and mixtures thereof. Other suitable plasticizing agents include triethylcitrate, tributylcitrate, and the like, and mixtures thereof. In a preferred embodiment, the plasticizing agent is selected from the group consisting of ethylene glycol, propylene glycol, acetyltributylcitrate, and mixtures thereof. In a more preferred embodiment, the plasticizing agent is propylene glycol.

The microcapsules of the present invention have a diameter under about 150 microns, preferably under about 100 microns, and most preferably under about 50 microns. The spray dried microcapsules formed in the present invention are spheroidal, that is, the microcapsules formed resemble spheres.

Once prepared, the chewable spray dried spheroidal microcapsule compositions may be used directly, may be stored for future use or may be formulated with conventional additives such as pharmaceutically acceptable carriers and confectionery bulking agents to prepare a wide variety of chewable taste masking medicament encapsulated compositions to suit particular applications. As set out above, while the inventive microcapsules have good taste masking properties, improve the mouth feel and overall chew characteristics of the medicament and improve the compressibility of sucralfate, these properties can be enhanced by incorporating the microcapsules into a pharmaceutically acceptable carrier or confectionery bulking agent such as tablet.

In this latter form of the invention, the taste masking composition includes the inventive chewable microcapsule compositions, a pharmaceutically acceptable carrier such as a confectionery bulking agent, and various additives. The confectionery may be in the form of a tablet, toffee, nougat, suspension, chewy candy, and the like. The pharmaceutically acceptable carriers may be prepared from a wide range of materials. Without being limited thereto, such materials include diluents, binding agents and adhesives, lubricants, disintegrants, coloring agents, bulking agents, flavoring agents, sweetening agents and miscellaneous materials such as buffers and adsorbents in order to prepare a particular medicated chewable confection.

In one embodiment, the invention is directed at a taste masking composition which comprises a therapeutically effective amount of a spray dried spheroidal microcapsule core under about 150 microns in diameter and a matrix over the core. In this embodiment, the taste masking composition is in the form of a compressed tablet confection which contains the microcapsules as particulate materials which are formed into structures under pressure. More particularly, the taste masking composition comprises:

(A) a microcapsule core comprising in percentages by weight of the core composition:

(a) sucralfate present in an amount from about 1% to about 70% and (b) a polymer soluble in the gastric fluids present in an amount from about 30% to about 99%; and (B) over the core comprising in percentages by weight of the matrix composition:

(a) a bulking agent present in an amount up to about 99.9%; and (b) a lubricating agent present in an amount from about 0.1% to about 7%.

In an alternative embodiment, the matrix of the coated microcapsule may further comprise a binding agent present in an amount from about 2% to about 15%, by weight of the matrix composition.

The bulking agent in the matrix is preferably present in the range up to about 99.9%, more preferably up to about 98%, and most preferably up to about 95%, by weight of the matrix composition.

The lubricating agent in the matrix is preferably present in the range from about 0.1% to about 7%, more preferably from about 0.5% to about 6%, and most preferably from about 1% to about 5%, by weight of the matrix composition.

The binding agent in the matrix, when present, is preferably present in an amount from about 2% to about 15%, more preferably in an amount from about 2% to about 10%, and most preferably from about 2% to about 5%, by weight of the matrix composition.

Suitable bulking agents in the present invention may be water-soluble and include sweetening agents selected from the group consisting of, but not limited to, monosaccharides, disaccharides, polysaccharides, sugar alcohols, and mixtures thereof; randomly bonded glucose polymers such as those polymers distributed under the tradename POLYDEXTROSE by Pfizer, Inc., Groton, Conn.; isomalt (a racemic mixture of alpha-D-glucopyranosyl-1,6-mannitol and alpha-D-glucopyranosyl-1,6-sorbitol manufactured under the tradename PALATINIT by Suddeutsche Zucker), maltodextrins; hydrogenated starch hydrolysates; hydrogenated hexoses; hydrogenated disaccharides; minerals, such as calcium carbonate, talc, titanium dioxide, dicalcium phosphate, celluloses, and the like, and mixtures thereof.

Suitable sugar bulking agents include monosaccharides, disaccharides and polysaccharides such as xylose, ribulose, glucose (dextrose), mannose, galactose, fructose (levulose), sucrose (sugar), maltose, invert sugar, partially hydrolyzed starch and corn syrup solids, and mixtures thereof. A preferred suitable sugar bulking agent is Di-Pac which is a co-crystallization mixture of 97% sucrose and 3% highly modified dextrines. Di-Pac and mixtures of sucrose and corn syrup solids are the more preferred sugar bulking agents.

Suitable sugar alcohol bulking agents include sorbitol, xylitol, mannitol, galactitol, maltitol, and mixtures thereof. Mixtures of sorbitol and mannitol are the preferred sugar alcohol bulking agents.

Maltitol is a sweet, water-soluble sugar alcohol useful as a bulking agent in the preparation of beverages and foodstuffs and is more fully described in U.S. Pat. No. 3,708,396, which disclosure is incorporated herein by reference. Maltitol is made by hydrogenation of maltose which is the most common reducing disaccharide and is found in starch and other natural products.

Suitable hydrogenated starch hydrolysates include those disclosed in U.S. Pat. Nos. Re. 25,959, 3,356,811, 4,279,931 and various hydrogenated glucose syrups and/or powders which contain sorbitol, hydrogenated disaccharides, hydrogenated higher polysaccharides, or mixtures thereof. Hydrogenated starch hydrolysates are primarily prepared by the controlled catalytic hydrogenation of corn syrups. The resulting hydrogenated starch hydrolysates are mixtures of monomeric, dimeric, and polymeric saccharides. The ratios of these different saccharides give different hydrogenated starch hydrolysates different properties. Mixtures of hydrogenated starch hydrolysates, such as LYCASIN, a commercially available product manufactured by Roquette Freres of France, and HYSTAR, a commercially available product manufactured by Lonza, Inc., of Fairlawn, N.J., are also useful.

In a preferred embodiment, the bulking agent is a sugar alcohol. In a more preferred embodiment, the bulking agent is a sugar alcohol selected from the group consisting of mannitol, sorbitol, and the like, and mixtures thereof. In a most preferred embodiment, the bulking agent is mannitol.

Suitable water-soluble lubricants include polyethylene glycol 4000 and 6000, sodium benzoate, and the like, and mixtures thereof. In a more preferred embodiment, the lubricating agent is a water-insoluble lubricant selected from the group consisting of, but not limited to, magnesium stearate, calcium stearate, zinc stearate, stearic acid, talc, waxes, and the like, and mixtures thereof. In a preferred embodiment, the lubricating agent is magnesium stearate.

Suitable binding agents, when present, may be selected from the group consisting of, but not limited to pregelatinized starch, sucrose, polyethylene glycol, and the like, and mixtures thereof. In a preferred embodiment, the binding agent is selected from the group consisting of pregelatinized starch, sucrose, and the like, and mixtures thereof.

In addition to the lubricant and binding agent components set out above, the compressed tablet confections may contain conventional tablet additives such as sweetening agents, flavoring agents, coloring agents, and the like.

The sweetening agents used may be selected from a wide range of materials including water-soluble sweeteners, water-soluble artificial sweeteners, water-soluble sweeteners derived from naturally occurring water-soluble sweeteners, dipeptide based sweeteners, and protein based sweeteners, including mixtures thereof. Without being limited to particular sweeteners, representative categories and examples include:

(a) water-soluble sweetening agents such as dihydrochalcones, monellin, steviosides, glycyrrhizin, dihydroflavenol, and sugar alcohols such as sorbitol, mannitol, maltitol, and L-aminodicarboxylic acid aminoalkenoic acid ester amides, such as those disclosed in U.S. Pat. No. 4,619,834, which disclosure is incorporated herein by reference, and the like, and mixtures thereof;

(b) water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (AcesulfameK), the free acid form of saccharin, and the like, and mixtures thereof;

(c) dipeptide based sweeteners, such as L-aspartic acid derived sweeteners, such as L-aspartyl-L-phenylalanine methyl ester (Aspartame) and materials described in U.S. Pat. No. 3,492,131, L-alpha-aspartyl-N-(2,2,4,4-tetramethyl-3-thietanyl)-D-alaninamide hydrate (Alitame), methyl esters of L-aspartyl-L-phenylglycerine and L-aspartyl-L-2,5-dihydrophenyl-glycine, L-aspartyl-2,5-dihydro-L-phenylalanine; L-aspartyl-L-(1-cyclohexen)-alanine, and the like, and mixtures thereof;

(d) water-soluble sweeteners derived from naturally occurring water-soluble sweeteners, such as chlorinated derivatives of ordinary sugar (sucrose), e.g., chlorodeoxysugar derivatives such as derivatives of chlorodeoxysucrose or chlorodeoxygalactosucrose, known, for example, under the product designation of Sucralose; examples of chlorodeoxysucrose and chlorodeoxyqalactosucrose derivatives include but are not limited to: 1-chloro-1'-deoxysucrose; 4-chloro-4-deoxy-alpha-D-galactopyranosyl-alpha-D-fructofuranoside, or 4-chloro-4-deoxygalactosucrose; 4-chloro-4-deoxy-alpha-D-galactopyranosyl-1-chloro-1-deoxy-beta-D-fructo-furanoside, or 4,1'-dichloro-4,1'-dideoxygalactosucrose; 1',6'-dichloro-1',6'-dideoxysucrose; 4-chloro-4-deoxy-alpha-D-galactopyranosyl-1,6-dichloro-1,6-dideoxy-beta-D-fructofuranoside, or 4,1',6'-trichloro-4,1',6'-trideoxygalactosucrose; 4,6-dichloro-4,6-dideoxy-alpha-D-galactopyranosyl-6-chloro-6-deoxy-beta-D-fructofuranoside, or 4,6,6'-trichloro-4,6,6'-trideoxygalactosucrose; 6,1',6'-trichloro-6,1',6'-trideoxysucrose; 4,6-dichloro-4,6-dideoxy-alpha-D-galactopyranosyl-1,6-dichloro-1,6-dideoxy-beta-D-fructofuranoside, or 4,6,1',6'-tetrachloro-4,6,1',6'-tetradeoxygalacto-sucrose; and 4,6,1$\alpha$,6'-tetrachloro-4,6,1',6'-tetradeoxy-sucrose, and mixtures thereof; and (e) protein based sweeteners such as thaumaoccous danielli (Thaumatin I and II).

The intense sweetening agents of the present invention may be used in many distinct physical forms well known in the art to provide an initial burst of sweetness and/or a prolonged sensation of sweetness. Without being limited thereto, such physical forms include free forms, such as spray dried, powdered, and beaded forms, and encapsulated forms, and mixtures thereof.

In general, an effective amount of sweetener is utilized to provide the level of sweetness desired, and this amount will vary with the sweetener selected. The amount of sweetener will normally be present in amounts from about 0.001% to about 3%, by weight of the composition, depending upon the sweetener used. The exact range of amounts for each type of sweetener is well known in the art and is not the subject of the present invention.

The flavoring agents which may be used include those flavors known to the skilled artisan, such as natural and artificial flavors. These flavorings may be chosen from synthetic flavor oils and flavoring aromatics and/or oils, oleoresins and extracts derived from plants, leaves, flowers, fruits, and so forth, and combinations thereof. Nonlimiting representative flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Also useful flavorings are artificial, natural and synthetic fruit flavors such as vanilla, and citrus oils including lemon, orange, lime, grapefruit, and fruit essences including apple, pear, peach, grape, strawberry, raspberry, cherry, plum, pineapple, apricot and so forth. These flavoring agents may be used in liquid or solid form and may be used individually or in admixture. Commonly used flavors include mints such as peppermint, menthol, artificial vanilla, cinnamon derivatives, and various fruit flavors, whether employed individually or in admixture.

Other useful flavorings include aldehydes and esters such as cinnamyl acetate, cinnamaldehyde, citral diethylacetal, dihydrocarvyl acetate, eugenyl formate, p-methylamisol, and so forth may be used. Generally any flavoring or food additive such as those described in *Chemicals Used in Food Processing,* publication 1274, pages 63-258, by the National Academy of Sciences, may be used.

Further examples of aldehyde flavorings include but are not limited to acetaldehyde (apple), benzaldehyde (cherry, almond), anisic aldehyde (licorice, anise), cinnamic aldehyde (cinnamon), citral, i.e., alpha-citral (lemon, lime), neral, i.e., beta-citral (lemon, lime), decanal (orange, lemon), ethyl vanillin (vanilla, cream), heliotrope, i.e., piperonal (vanilla, cream), vanillin (vanilla, cream), alpha-amyl cinnamaldehyde (spicy fruity flavors), butyraldehyde (butter, cheese), valeraldehyde (butter, cheese), citronellal (modifies, many types), decanal (citrus fruits), aldehyde C-8 (citrus fruits), aldehyde C-9 (citrus fruits), aldehyde C-12 (citrus fruits), 2-ethyl butyraldehyde (berry fruits), hexenal, i.e., trans-2 (berry fruits), tolyl aldehyde (cherry, almond), veratraldehyde (vanilla), 2,6-dimethyl-5-heptenal, i.e., melonal (melon), 2,6-dimethyloctanal (green fruit), and 2-dodecenal (citrus, mandarin), cherry, grape, strawberry shortcake, mixtures thereof and the like.

The flavoring agent may be employed in either liquid form and/or dried for.. When employed in the latter form, suitable drying means such as spray drying the oil may be used. Alternatively, the flavoring agent may be absorbed onto water soluble materials, such as cellulose, starch, sugar, maltodextrin, gum arabic and so forth or may be encapsulated. The actual techniques for preparing such dried forms are well known and do not constitute a part of this invention.

The flavoring agents of the present invention may be used in many distinct physical forms well known in the art to provide an initial burst of flavor and/or a prolonged sensation of flavor. Without being limited thereto, such physical forms include free forms, such as spray dried, powdered, and beaded forms, and encapsulated forms, and mixtures thereof.

The amount of flavoring agent employed herein is normally a matter of preference subject to such factors as the type of final composition, the individual flavor, and the strength of flavor desired. Thus, the amount of flavoring may be varied in order to obtain the result desired in the final product and such variations are within the capabilities of those skilled in the art without the need for undue experimentation. In tablet compositions, the flavoring agent is generally present in amounts from about 0.02% to about 5%, and preferably from about 0.1% to about 2%, and more preferably, from about 0.8% to about 1.8%, by weight of the composition.

The coloring agents useful in the present invention are used in amounts effective to produce the desired color. These coloring agents include pigments which may be incorporated in amounts up to about 6%, by weight of the composition. A preferred pigment, titanium dioxide, may be incorporated in amounts up to about 2%, and preferably less than about 1%, by weight of the gum composition. The colorants may also include natural food colors and dyes suitable for food, drug and cosmetic applications. These colorants are known as F.D.& C. dyes and lakes. The materials acceptable for the foregoing uses are preferably water-soluble. Illustrative nonlimiting examples include the indigoid dye known as F.D.& C. Blue No.2, which is the disodium salt of 5,5-indigotindisulfonic acid. Similarly, the dye known as F.D.& C. Green No.1 comprises a triphenylmethane dye and is the monosodium salt of 4-[4-(N-ethyl-p-sulfoniumbenzylamino) diphenylmethylene]-[1-(N-ethyl -N-p-sulfoniumbenzyl)-delta-2,5-cyclohexadieneimine]. A full recitation of all F.D.& C. colorants and their corresponding chemical structures may be found in the Kirk-Othmer Encyclopedia of Chemical Technology, 3rd Edition, in volume 5 at pages 857–884, which text is incorporated herein by reference.

The weight ratio of microcapsule core composition to matrix composition is the ratio containing sufficient matrix to prevent potential premature release of sucralfate from the microcapsule core without forming a composition so large so as to be therapeutically unsuitable for use in chewable compositions. In general, the weight ratio of microcapsule core composition to matrix composition is from about 1:9 to about 9:1, preferably from about 1:4 to about 1:1, and more preferably from about 1:4 to about 1:2, respectively.

An important aspect of the present invention includes a hard or soft confectionery composition incorporating the inventive sucralfate microcapsule composition and a method for preparing the hard or soft confections. In this form of the invention, the taste masking composition includes a pharmaceutically acceptable carrier such as a confectionery bulking agent, the inventive sucralfate microcapsule composition, and various additives. The confectionery may be in the form of a lozenge, toffee, nougat, suspension, chewy candy, and the like. The pharmaceutically acceptable carriers may be prepared from a wide range of materials. Without being limited thereto, such materials include diluents, binding agents and adhesives, lubricants, disintegrants, coloring agents, bulking agents, flavoring agents, sweetening agents and miscellaneous materials such as buffers and adsorbents in order to prepare a particular taste masking confection.

The preparation of confectionery formulations is historically well known and has changed little through the years. Confectionery items have been classified as either "hard" confectionery or "soft" confectionery. The sucralfate microcapsule compositions of the present invention can be incorporated into confectionery compositions by admixing the inventive composition into conventional hard and soft confections.

As used herein, the term confectionery material means a product containing a bulking agent selected from a wide variety of materials such as sugar, corn syrup, and in the case of sugarless bulking agents, sugar alcohols such as sorbitol and mannitol and mixtures thereof. Confectionery material may include such exemplary substances as lozenges, tablets, toffee, nougat, suspensions, chewy candy, chewing gum and the like. The bulking agent is present in a quantity sufficient to bring the total amount of composition to 100%.

Lozenges are flavored medicated dosage forms intended to be sucked and held in the mouth. Lozenges may be in the form of various shapes such as flat, circular, octagonal and biconvex forms. The lozenge bases are generally in two forms: hard, boiled candy lozenges and compressed tablet lozenges.

Hard boiled candy lozenges may be processed and formulated by conventional means. In general, a hard boiled candy lozenge has a base composed of a mixture of sugar and other carbohydrate bulking agents kept in an amorphous or glassy condition. This amorphous or glassy form is considered a solid syrup of sugars generally having from about 0.5% to about 1.5% moisture. Such materials normally contain up to about 92% corn syrup, up to about 55% sugar and from about 0.1% to about 5% water, by weight of the final composition. The syrup component is generally prepared from corn syrups high in fructose, but may include other materials. Further ingredients such as flavoring agents, sweetening agents, acidulants, coloring agents and the like may also be added.

Boiled candy lozenges may also be prepared from non-fermentable sugars such as sorbitol, mannitol, and hydrogenated corn syrup. Typical hydrogenated corn syrups are Lycasin, a commercially available product manufactured by Roquette Corporation, and Hystar, a commercially available product manufactured by Lonza, Inc. The candy lozenges may contain up to about 95% sorbitol, a mixture of sorbitol and mannitol in a ratio from about 9.5:0.5 up to about 7.5:2.5, and hydrogenated corn syrup up to about 55%, by weight of the solid syrup component.

Boiled candy lozenges may be routinely prepared by conventional methods such as those involving fire cookers, vacuum cookers, and scraped-surface cookers also referred to as high speed atmospheric cookers.

Fire cookers involve the traditional method of making a boiled candy lozenge base. In this method, the desired quantity of carbohydrate bulking agent is dissolved in water by heating the agent in a kettle until the bulking agent dissolves. Additional bulking agent may then be added and cooking continued until a final temperature of 145° C. to 156° C. is achieved. The batch is then cooled and worked as a plastic-like mass to incorporate additives such as flavors, colorants and the like.

A high-speed atmospheric cooker uses a heat-exchanger surface which involves spreading a film of candy on a heat exchange surface, the candy is heated to 165° C. to 170° C. in a few minutes. The candy is then rapidly cooled to 100° C. to 120° C. and worked as a plastic-like mass enabling incorporation of the additives, such as flavors, colorants and the like.

In vacuum cookers, the carbohydrate bulking agent is boiled to 125° C. to 132° C., vacuum is applied and additional water is boiled off without extra heating. When cooking is complete, the mass is a semi-solid and has a plastic-like consistency. At this point, flavors, colorants, and other additives are admixed in the mass by routine mechanical mixing operations.

The optimum mixing required to uniformly mix the flavoring agents, coloring agents and other additives during conventional manufacturing of boiled candy lozenges is determined by the time needed to obtain a uniform distribution of the materials. Normally, mixing times of from 4 to 10 minutes have been found to be acceptable.

Once the boiled candy lozenge has been properly tempered, it may be cut into workable portions or formed into desired shapes. A variety of forming techniques may be utilized depending upon the shape and size of the final product desired. A general discussion of the composition and preparation of hard confections may be found in H. A. Lieberman, *Pharmaceutical Dosage Forms: Tablets,* Volume 1 (1980), Marcel Dekker, Inc., New York, N.Y. at pages 339 to 469, which disclosure is incorporated herein by reference.

The apparatus useful in accordance with the present invention comprises cooking and mixing apparatus well known in the confectionery manufacturing arts, and therefore the selection of the specific apparatus will be apparent to the artisan.

In addition to hard confectionery materials, the lozenges of the present invention may be made of soft confectionery materials such as those contained in nougat. The preparation of soft confections, such as nougat, involves conventional methods, such as the combination of two primary components, namely (1) a high boiling syrup such as a corn syrup, hydrogenated starch hydrolysate or the like, and (2) a relatively light textured frappe, generally prepared from egg albumin, gelatin, vegetable proteins, such as soy derived compounds, sugarless milk derived compounds such as milk proteins, and mixtures thereof. The frappe is generally relatively light, and may, for example, range in density from about 0.5 to about 0.7 grams/cc.

The high boiling syrup, or "bob syrup" of the soft confectionery is relatively viscous and has a higher density than the frappe component, and frequently contains a substantial amount of carbohydrate bulking agent such as a hydrogenated starch hydrolysate. Conventionally, the final nougat composition is prepared by the addition of the "bob syrup" to the frappe under agitation, to form the basic nougat mixture. Further ingredients such as flavoring agents, additional carbohydrate bulking agent, coloring agents, preservatives, medicaments, mixtures thereof and the like may be added thereafter also under agitation. A general discussion of the composition and preparation of nougat confections may be found in B. W. Minifie, *Chocolate, Cocoa and Confectionery:* Science and Technology, 2nd edition, AVI Publishing Co., Inc., Westport, Conn. (1980), at pages 424–425, which disclosure is incorporated herein by reference.

The procedure for preparing the soft confectionery involves known procedures. In general, the frappe component is prepared first and thereafter the syrup component is slowly added under agitation at a temperature of at least about 65° C., and preferably at least about 100° C. The mixture of components is continued to be mixed to form a uniform mixture, after which the mixture is cooled to a temperature below 80° C., at which point, the flavoring agent may be added. The mixture is further mixed for an additional period until it is ready to be removed and formed into suitable confectionery shapes.

The novel chewable medicated microcapsules and taste masking compositions may also be in the form of a pharmaceutical suspension. Pharmaceutical suspensions of this invention may be prepared by conventional methods long established in the art of pharmaceutical compounding. Suspensions may contain adjunct materials employed in formulating the suspensions of the art. The suspensions of the present invention can comprise:

(a) preservatives such as benzoic acid, sorbic acid, methyl paraben, and propyl paraben. Preservatives are generally present in amounts up to about 1%, and preferably from about 0.05% to about 0.5%, by weight of the suspension;

(b) buffers such as citric acid-sodium citrate, phosphoric acid-sodium phosphate, and acetic acid-sodium acetate which may be present in amounts up to about 1%, and preferably from about 0.05% to about 0.5%, by weight of the suspension;

(c) suspending agents or thickeners such as cellulosics like methylcellulose, carrageenans like alginic acid and its derivatives, xanthan gums, gelatin, acacis, and microcrystalline cellulose which may be present in amounts up to about 20%, and preferably from about 1% to about 15%, by weight of the suspension;

(d) antifoaming agents such as dimethyl polysiloxane which may be present in amounts up to about 0.2%, and preferably from about 0.01% to about 0.1%, by weight of the suspension;

(e) sweetening agents such as those sweeteners well known in the art, including both natural and artificial sweeteners. Sweetening agents such as monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, steviosides, glycyrrhizin, and sugar alcohols such as sorbitol, mannitol, maltitol, hydrogenated starch hydrolysates and mixtures thereof may be utilized in amounts up to about 60%, and preferably from about 20% to about 50%, by weight of the suspension. Water-soluble artificial sweeteners such as soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (Acesulfame-K), the free acid form of saccharin, and the like may be utilized in amounts from about 0.001% to about 5%, by weight of the suspension;

(f) flavoring agents such as those flavors well known to the skilled artisan, such as natural and artificial flavors and mints, such as peppermint, menthol, citrus flavors such as orange and lemon, artificial vanilla, cinnamon, various fruit flavors, both individual and mixed and the like may be utilized in amounts from about 0.5% to about 5%, by weight of the suspension;

(g) coloring agents such as pigments which may be incorporated in amounts up to about 6%, by weight of the suspension. A preferred pigment, titanium dioxide, may be incorporated in amounts up to about 2%, and preferably less than about 1%, by weight of the suspension. The coloring agents may also include natural food colors and dyes suitable for food, drug and cosmetic applications. These coloring agents are known as F.D.& C. dyes and lakes. The materials acceptable for the foregoing uses are preferably water-soluble. Such dyes are generally present in amounts up to about 0.25%, and preferably from about 0.05% to about 0.2%, by weight of the suspension;

(h) decolorizing agents such as sodium metabisulfite, ascorbic acid and the like may be incorporated into the suspension to prevent color changes due to aging. In general, decolorizing agents may be used in amounts up to about 0.25%, and preferably from about 0.05% to about 0.2%, by weight of the suspension; and (i) vehicles such as alcohol, propylene glycol, polyethylene glycol, edible oils such as animal, vegetable and mineral oils, and the like may be used to solubilize the flavoring agents. In general, vehicles may be used in amounts up to about 10%, and preferably from about 2% to about 5%, by weight of the suspension.

The pharmaceutical suspensions of the present invention may be prepared as follows:

(A) admix the thickener with the vehicle heated to a temperature from about 40° C. to about 95° C., preferably from about 40° C. to about 70° C., to form a dispersion if the thickener is soluble in the vehicle or a solution if the thickener is soluble in the soluble;

(B) admix the sweetening agent with the vehicle to form a solution;

(C) admix the sustained release composition with the thickener-vehicle admixture to form a uniform thickener-sustained release composition;

(D) combine the sweetener solution with the thickener-sustained release composition and mix until uniform; and (E) admix the optional adjunct materials such as coloring agents, flavoring agents, decolorants, solubilizing agents, antifoaming agents, buffers and additional vehicle with the mixture of step (D) to form the suspension.

The taste masking compositions of this invention may be in chewable form. To achieve acceptable stability and quality as well as good taste and mouth feel in a chewable formulation several considerations are important. These considerations include the amount of active substance per tablet, the flavoring agent employed, the degree of compressibility of the tablet and the organoleptic properties of the composition.

Chewable taste masking candy is prepared by procedures similar to those used to make soft confectionery. In a typical procedure, a boiled sugar-corn syrup blend is formed to which is added a frappe mixture. The boiled sugar-corn syrup blend may be prepared from sugar and corn syrup blended in parts by weight ratio of about 90:10 to about 10:90. The sugar-corn syrup blend is heated to temperatures above about 120° C. to remove water and to form a molten mass. The frappe is generally prepared from gelatin, egg albumin, milk proteins such as casein, and vegetable proteins such as soy protein, and the like, which is added to a gelatin solution and rapidly mixed at ambient temperature to form an aerated sponge like mass. The frappe is then added to the molten candy mass and mixed until homogeneous at temperatures between about 65° C. and about 120° C.

The sucralfate microcapsule composition of the instant invention can then be added to the homogeneous mixture as the temperature is lowered to about 65° C.–95° C. whereupon additional ingredients can then be added such as flavoring agents and coloring agents. The formulation is further cooled and formed into pieces of desired dimensions.

A general discussion of the lozenge and chewable tablet forms of confectionery may be found in H. A. Lieberman and L. Lachman, *Pharmaceutical Dosage Forms: Tablets* Volume 1, Marcel Dekker, Inc., New York, N.Y. at pages 289 to 466, which disclosure is incorporated herein by reference.

In accordance with this invention, therapeutically effective amounts of the chewable microcapsule compositions of the present invention may be admixed into the hard and soft confections. These amounts are readily determined by those skilled in the art without the need for undue experimentation.

The present invention extends to methods of making the improved chewable medicated hard and soft confection compositions. The medicated microcapsule compositions may be incorporated into otherwise conventional hard or soft confection compositions using standard techniques and equipment known to those skilled in the art.

The apparatus useful in accordance with the present invention comprises cooking and mixing apparatus well known in the confectionery manufacturing arts, and therefore the selection of the specific apparatus will be apparent to the artisan.

The present invention is also directed at a method for preparing spray dried spheroidal microcapsules under about 150 microns in diameter, which comprises the steps of:

(A) providing the following ingredients, in percentages by weight of the microcapsule composition:

(a) sucralfate present in an amount from about 1% to about 70%; and (b) a polymer soluble in the gastric fluids present in an amount from about 30% to about 99%; and (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and (C) feeding the mixture of step (B) into a spray dryer and spray drying the mixture under controlled conditions such that spheroidal microcapsules under about 150 microns in diameter are formed.

The concentration of the aqueous mixture of sucralfate in step (B) is sufficiently dilute to prevent coagulation of sucralfate. In a preferred embodiment, the concentration of sucralfate in step (B) is from about 1% to about 60%, preferably from about 1% to about 50%, and most preferably from about 1% to about 40%, by weight of the aqueous mixture.

The concentration of the aqueous mixture of the polymer soluble in the gastric fluids in step (B) is sufficiently dilute to prevent coagulation of the polymer soluble in the gastric fluids. In a preferred embodiment, the concentration of the polymer soluble in the gastric fluids in step (B) is from about 5% to about 60%, preferably from about 5% to about 50%, and most preferably from about 5% to about 40%, by weight of the aqueous mixture.

The aqueous homogeneous mixture of step (B) in the method of the present invention is spray dried in step (C) under controlled conditions such that the mixture is flash dried and spheroidal microcapsules of under about 150 microns in diameter are formed. Flash drying (the rapid evaporation of solvent) involves the optimizing of various parameters in the spray drying process such as the liquid feed rate, the air flow rate, the nozzle setting, the pressure of the system and the air inlet and air outlet temperatures. For example, the air outlet temperature must be sufficiently high so that sufficient heat is available to rapidly dry the spray and form small spheroidal microcapsules. The air outlet temperature is dependent upon such other parameters as the air inlet temperature and the liquid feed rate. The aqueous mixture of the present invention may be flash dried using standard techniques and equipment known to those skilled in the art. The exact conditions for flash drying will vary with the particular apparatus selected and are readily determined by those skilled in the art without the need for undue experimentation. Spray drying apparatus is well known in the arts and therefore the selection of the specific apparatus will be apparent to the artisan.

In a preferred embodiment, the spray drying apparatus is a Buchi spray dryer, such as a Buchi 190 Mini Spray dryer. In this embodiment, the liquid feed rate is preferably from about 5 ml/min. to about 25 ml/min., more preferably from about 7 ml/min. to about 22 ml/min., and most preferably from about 9 ml/min. to about 20 ml/min. The air flow rate is preferably from about 300 Nl/h (normliters per hour) to about 750 Nl/h, and more preferably from about 400 Nl/h to about 700 Nl/h, and most preferably from about 500 Nl/h to about 700 Nl/h. The nozzle setting is preferably from about 0.8 mm to about 2.0 mm, more preferably from about 0.8 mm to about 1.5 mm, and most preferably from about 1 mm to about 1.5 mm. The pressure of the system (system pressure) is preferably from about 25 mm/Hg to about 50 mm/Hg, more preferably from about 30 mm/Hg to about 50 mm/Hg, and most preferably from about 35 mm/Hg to about 50 mm/Hg. The air inlet temperature of the spray dryer is preferably from about 60° C. to about 145° C., more preferably from about 80° C. to about 140° C., and most preferably from about 85° C. to about 135° C. The air outlet temperature of the spray dryer is preferably from about 40° C. to about 90° C., more preferably from about 45° C. to about 90° C., and most preferably from about 50° C. to about 80° C.

In another embodiment, the present invention is directed at a method for preparing a taste masking composition which comprises a therapeutically effective amount of a spray dried spheroidal microcapsule core under about 150 microns in diameter and a matrix over the core which comprises the steps of:

(A) providing the following ingredients of the microcapsule core in percentages by weight of the core composition:

(a) sucralfate present in an amount from about 1% to about 70%; and (b) a polymer soluble in the gastric fluids present in an amount from about 30% to about 99%; and (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and (C) feeding the mixture of step (B) into a spray dryer and spray drying the mixture under controlled conditions such that spheroidal microcapsules under about 150 microns in diameter are formed;

(D) providing the following ingredients of the matrix, in percentages by weight of the matrix composition:

(a) a bulking agent present in an amount up to about 99.9%; and (b) a lubricating agent present in an amount from about 0.1% to about 7%; and (E) preparing a homogeneous mixture of the ingredients in step (D); and (F) preparing a homogeneous mixture of the spray dried microcapsules from step (C) and the matrix mixture from step (E) and compressing the homogeneous mixture into tablets.

In this embodiment, the spray dried spheroidal microcapsules from step (C) are thoroughly mixed with the matrix mixture from step (E) and compressed into tablets. The microcapsules may be compressed into tablets using standard techniques and equipment known to those skilled in the art. The exact conditions for forming tablets will vary with the particular tablet press selected and are readily determined by those skilled in the art without the need for undue experimentation. Tablet presses are well known in the art and therefore the selection of the specific apparatus will be apparent to the artisan.

In another embodiment, the present invention is directed a method for preparing a taste masking composition which comprises a pharmaceutically acceptable carrier and a therapeutically effective amount of a spray dried spheroidal microcapsule core under about 150 microns in diameter which comprises the steps of:

(A) providing the following ingredients, in percentages by weight of the microcapsule composition:
   (a) sucralfate present in an amount from about 1% to about 70%: and
   (b) a polymer soluble in the gastric fluids present in an amount from about 30% to about 99%; and (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and (C) feeding the mixture of step (B) into a spray dryer and spray drying the mixture under controlled conditions such that spheroidal microcapsules under about 150 microns in diameter are formed;

(D) heating and mixing the pharmaceutically acceptable carrier in water at an elevated temperature;

(E) cooling the pharmaceutically acceptable carrier to a temperature below about 120° C.;

(F) preparing a homogeneous mixture of the spray dried microcapsules from step (C) and the pharmaceutically acceptable carrier from step (E); and (G) forming the resulting mixture into shapes.

In another embodiment, the present invention is directed at spray dried spheroidal microcapsules under about 150 microns in diameter prepared by a method which comprises the steps of:

(A) providing the following ingredients, in percentages by weight of the microcapsule composition:
   (a) sucralfate present in an amount from about 1% to about 70%; and
   (b) a polymer soluble in the gastric fluids present in an amount from about 30% to about 99%; and (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and (C) feeding the mixture of step (B) into a spray dryer and spray drying the mixture under controlled conditions such that spheroidal microcapsules under about 150 microns in diameter are formed.

In another embodiment, the present invention is directed at a taste masking composition which comprises a therapeutically effective amount of a spray dried spheroidal microcapsule core under about 150 microns in diameter and a matrix over the core prepared by a method which comprises the steps of:

(A) providing the following ingredients of the microcapsule core in percentages by weight of the core composition:
   (a) sucralfate present in an amount from about 1% to about 70%; and
   (b) a polymer soluble in the gastric fluids present in an amount from about 30% to about 99%; and (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and (C) feeding the mixture of step (B) into a spray dryer and spray drying the mixture under controlled conditions such that spheroidal microcapsules under about 150 microns in diameter are formed;

(D) providing the following ingredients of the matrix, in percentages by weight of the matrix composition:
   (a) bulking agent present in an amount up to about 99.9%; and
   (b) a lubricating agent present in an amount from about 0.1% to about 7%; and (E) preparing a homogeneous mixture of the ingredients in step (D); and (F) preparing a homogeneous mixture of the spray dried microcapsules from step (C) and the matrix mixture from step (E) and compressing the homogeneous mixture into tablets.

The present invention is further illustrated by the following examples which are not intended to limit the effective scope of the claims. All parts and percentages in the examples and throughout the specification and claims are by weight of the final composition unless otherwise specified.

EXAMPLE 1

This Example demonstrates a method for preparing spray dried spheroidal microcapsules according to the process of the present invention.

A spray dried spheroidal microcapsule or core particle was prepared having the composition set out in Table 1.

TABLE 1

| SPRAY DRIED MICROCAPSULE COMPOSTION | | | |
|---|---|---|---|
| INGREDIENT | AMOUNT | % BY WEIGHT MICROCAPSULE | % BY WEIGHT AQUEOUS MIXTURE |
| Sucralfate | 250 g | 50 | 10.78 |
| Maltrin | 250 g | 50 | 10.78 |
| Distilled water | 1820 ml | | |

Maltrin was dissolved in the water and then sucralfate was suspended in the maltrin solution with constant mixing. The resulting suspension was spray dried in a Buchi 190 Mini Spray dryer wherein the liquid feed rate was 15 ml/minute, the air flow rate was 600 Nl/h, the nozzle setting was 1.2 mm, the system pressure was 45 mm/Hg, the air inlet temperature was from about 90° C. to about 110° C., and the air outlet temperature was from about 55° C. to about 61° C. A quantity of 400g of the spray dried microcapsules containing sucralfate were obtained which were passed through a 100 mesh screen (greater than about 90% of the microcapsules passed through the screen).

FIG. 1 is a picture of the spray dried spheroidal microcapsules of sucralfate and maltodextrin (magnification 100X) prepared in this manner. The spheroidal appearance is clearly seen.

The sucralfate-maltrin microcapsules had good flow and good taste. The sucralfate microcapsules could be compressed directly into tablets having good taste masking properties.

EXAMPLES 2-6

These Examples demonstrate methods for preparing taste masking compositions according to the process of the present invention.

A taste masking composition was prepared having the composition set out in Table 2.

TABLE 2

| TASTE MASKING COMPOSITION | | |
|---|---|---|
| INGREDIENT | AMOUNT | PERCENTAGE BY WEIGHT MATRIX |
| Sucralfate Microcapsules | 1.0 g | |
| Mannitol | 0.25 g | 95.24 |
| Magnesium Stearate | 0.0125 g | 4.76 |

The microcapsule core material prepared in Example 1 was mixed uniformly with the mannitol and magnesium stearate and then transferred into a 0.5 inch tablet press and compressed into tablets. The tablets prepared had good taste masking properties.

Five different Examples (2-6) of taste masking compositions were prepared. Each Example had the composition set out in Table 2 and each Example was compressed into a tablet using the force (in lbs.) and compression time (in seconds) set out in Table 3. The hardness or crushing strength of each tablet Example was determined using a Schleuniger apparatus, also known as the Heberlein, distributed by the Vector Corporation. The force required to break the tablet is set out in Table 3 expressed in kilograms of force (Kp).

TABLE 3

| COMPRESSIBILITY OF TASTE MASKING COMPOSITIONS | | | |
|---|---|---|---|
| EXAMPLE | COMPRESSION TIME (SECONDS) | COMPRESSION FORCE (LBS) | TABLET HARDNESS (Kp) |
| 2 | 5 | 1500 | 6.0 |
| 3 | 10 | 3000 | 20.0 |
| 4 | 10 | 2000 | 12.0 |
| 5 | 10 | 2000 | 12.0 |
| 6 | 10 | 2000 | 12.0 |

Table 3 shows that sucralfate microcapsules can be compressed with mannitol into tablets having satisfactory hardness.

EXAMPLES 7-8

These Examples demonstrate another method for preparing a taste masking composition according to the process of the present invention.

A taste masking composition was prepared having the composition set out in Table 4.

TABLE 4

| TASTE MASKING COMPOSITION | |
|---|---|
| INGREDIENT | AMOUNT |
| Sucralfate Microcapsules | 1.0 g |
| Di-Pac | 0.25 g |
| Magnesium Stearate | 0.0125 g |

The microcapsule core material prepared in Example 1 was mixed uniformly with the Di-Pac (97% sucrose and 3% highly modified dextrines) and magnesium stearate and then transferred into a 0.5 inch tablet press and compressed into tablets. The tablets prepared had good taste masking properties.

Two Examples (7-8) of taste masking compositions were prepared. Each Example had the composition set out in Table 5 and each Example was compressed into a tablet using the compression force (in lbs.) and compression time (in seconds) set out in Table 5. The hardness or crushing strength of each tablet Example was determined using a Schleuniger apparatus. The force required to break the tablet is set out in Table 5 expressed in kilograms of force (Kp).

TABLE 5

| COMPRESSIBILITY OF TASTE MASKING COMPOSITIONS | | | |
|---|---|---|---|
| EXAMPLE | COMPRESSION TIME (SECONDS) | COMPRESSION FORCE (LBS) | TABLET HARDNESS (Kp) |
| 7 | 10 | 3000 | 20.0 |
| 8 | 10 | 2000 | 14.4 |

Table 5 shows that sucralfate microcapsules can be compressed with Di-Pac into tablets having satisfactory hardness.

EXAMPLES 9-10

These Examples demonstrate another method for preparing a taste masking composition according to the process of the present invention.

A taste masking composition was prepared having the composition set out in Table 6.

TABLE 6

| TASTE MASKING COMPOSITION | |
|---|---|
| INGREDIENT | AMOUNT |
| Sucralfate Microcapsules | 1.0 g |
| Sugar Confectionery | 0.25 g |
| Magnesium Stearate | 0.0125 g |

The microcapsule core material prepared in Example 1 was mixed uniformly with the sugar confectionery (sucrose) and magnesium stearate and then transferred into a 0.5 inch tablet press and compressed into tablets. The tablets prepared had good taste masking properties.

Two Examples (9-10) of taste masking compositions were prepared. Each Example had the composition set out in Table 6 and each Example was compressed into a tablet using the compression force (in lbs.) and compression time (in seconds) set out in Table 7. The hardness or crushing strength of each tablet Example was determined using a Schleuniger apparatus. The force required to break the tablet is set out in Table 7 expressed in kilograms of force (Kp).

TABLE 7

| COMPRESSIBILITY OF TASTE MASKING COMPOSITIONS | | | |
|---|---|---|---|
| EXAMPLE | COMPRESSION TIME (SECONDS) | COMPRESSION FORCE (LBS) | TABLET HARDNESS (Kp) |
| 9 | 10 | 2000 | 10.0 |
| 10 | 10 | 2500 | 13.6 |

Table 7 shows that sucralfate microcapsules can be compressed with sugar into tablets having satisfactory hardness.

EXAMPLES 11-18

These Examples demonstrate a comparison of the compressibility of taste masking compositions prepared according to the process of the present invention versus bulking agents and compression force.

Taste masking compositions were prepared having the compositions set out in Table 8.

TABLE 8

TASTE MASKING COMPOSITIONS

| EXAMPLE | Sucralfate Microcapsules | Bulking Agent | Magnesium Stearate |
|---|---|---|---|
| 11 | 1.0 g | — | 10 mg |
| 12 | 1.0 g | — | 10 mg |
| 13 | 1.0 g | 0.5 g Di-pac | 10 mg |
| 14 | 1.0 g | 0.25 g Di-pac | 10 mg |
| 15 | 1.0 g | 0.25 g Di-pac | 10 mg |
| 16 | 1.0 g | 1.5 g Di-pac | — |
| 17 | 1.0 g | 1.5 g Di-pac | 25 mg |
| 18 | 1.0 g | 0.5 g Di-pac | — |

The microcapsule core material prepared in Example 1 was mixed uniformly with the Di-Pac, when present, and magnesium stearate, when present, and then transferred into a 0.5 inch tablet press and compressed into tablets. The tablets prepared had good taste masking properties.

Each Example was compressed into a tablet during a compression time of 10 seconds using the force (in lbs.) set out in Table 9. The hardness or crushing strength of each tablet Example was determined using a Schleuniger apparatus. The force required to break the tablet is set out in Table 9 expressed in kilograms of force (Kp).

TABLE 9

COMPRESSIBILITY OF TASTE MASKING COMPOSITIONS

| EXAMPLE | COMPRESSION FORCE (LBS) | TABLET HARDNESS (Kp) |
|---|---|---|
| 11 | 3000 | no break |
| 12 | 1500 | 20 |
| 13 | 1500 | 16.2 |
| 14 | 1000 | 15.6 |
| 15 | 1000 | 14.4 |
| 16 | 4000 | 15.5 |
| 17 | 3000 | 12.8 |
| 18 | 3000 | 14.6 |

Table 9 shows that sucralfate microcapsules can be compressed without bulking agent into tablets having satisfactory hardness (Examples 11 and 12). Table 9 also shows that sucralfate microcapsules can be compressed with Di-Pac into tablets having satisfactory hardness (Examples 13 through 18).

EXAMPLES 19–25

These Examples demonstrate a comparison of taste masking properties of compositions prepared according to the process of the present invention.

Taste masking compositions (Examples 19–25) were prepared having the compositions set out in Table 10.

TABLE 10

TASTE MASKING COMPOSITIONS

| EXAMPLE | Sucralfate | Bulking Agent | Magnesium powder |
|---|---|---|---|
| 19 | 10.0 g microcapsules | 2.5 g Di-pac | 0.067 g |
| 20 | 20.0 g microcapsules | 20.0 g Di-pac | 0.020 g |
| 21 | 20.0 g microcapsules | 20.0 g mannitol | 0.020 g |
| 22 | 10.0 g microcapsules | 2.5 g mannitol | 0.064 g |
| 23 | 12.5 g powder | 12.5 g mannitol | 0.125 g |
| 24 | 25.0 g powder | 25.0 g starch 1500 | 0.25 g |
| 25 | 10.0 g | 12.5 g Di-pac | 0.11 g |

Examples 19–25 were prepared by uniformly mixing Sucralfate microcapsule core material, prepared as in Example 1 (50% loading), or Sucralfate powder, with the bulking agent and magnesium stearate, as set out in Table 10, and then transferring the mixture into a 0.5 inch tablet press and compressing the mixture into tablets.

An expert taste panel evaluated the relative astringency of the tablets having the compositions of Examples 19–25 (on a scale of 1–9, 1 being not astringent, and 9 being very astringent) in random order and the findings were pooled and averaged. The astringency of the tablets was determined (A) holding the tablet in the mouth (unchewed), (B) chewing the tablet (chewed), and (C) after chewing the tablet (aftertaste). The results from the taste panel are set out in Table 11.

TABLE 11

EVALUATION OF TASTE MASKING COMPOSITIONS

| EXAMPLE | A | B | C |
|---|---|---|---|
| 19 | 1.0 | 1.0 | 1.0 |
| 20 | 1.0 | 1.0 | 1.0 |
| 21 | 1.0 | 1.0 | 1.0 |
| 22 | 1.0 | 1.0 | 1.0 |
| 23 | 6.4 | 7.2 | 7.8 |
| 24 | 6.8 | 7.0 | 7.0 |
| 25 | 4.8 | 5.4 | 4.8 |

Table 11 shows that the astringent taste of Sucralfate is effectively masked in Examples 19–22 when Sucralfate microcapsules are incorporated into the tablet. The astringent taste of Sucralfate is not effectively masked in Examples 23–25 when Sucralfate in powder form is incorporated into the tablet.

The invention being thus described, it will be obvious that the same may be varied in many ways. Such variations are not to be regarded as a departure from the spirit and scope of the invention and all such modifications are intended to be included within the scope of the following claims.

I claim:

1. A spray dried spheroidal microcapsule under about 150 microns in diameter which comprises in percentages by weight of the microcapsule composition:
   (a) sucralfate present in an amount from about 1% to about 70%; and
   (b) a polymer soluble in the gastric fluids present in an amount from about 30% to about 99%.

2. The microcapsule according to claim 1, wherein sucralfate is present in an amount from about 1% to about 60%, by weight of the microcapsule composition.

3. The microcapsule according to claim 1, wherein the polymer soluble in the gastric fluids is present in an amount from about 40% to about 99%, by weight of the microcapsule composition.

4. The microcapsule according to claim 1, wherein the polymer soluble in the gastric fluids is selected from the group consisting of maltodextrins, gelatin, acacia, agar, alginic acid, carrageenan, guar, pectin, tragacanth, xanthan, carboxymethyl cellulose, methyl cellulose, microcrystalline cellulose, polyacrylic acid, polyvinyl alcohol, polyvinyl pyrrolidone polymers, and mixtures thereof.

5. The microcapsule according to claim 4, wherein the polymer soluble in the gastric fluids is selected from the group consisting of maltodextrins, gelatin, alginic acid, and mixtures thereof.

6. The microcapsule according to claim 1, further comprising a plasticizing agent present in an amount from about 5% to about 30%, by weight of the microcapsule composition.

7. The microcapsule according to claim 6, wherein the plasticizing agent is selected from the group consisting of ethylene glycol, propylene glycol, acetyltributylcitrate, and mixtures thereof.

8. The microcapsule according to claim 1, wherein the microcapsule is under about 100 microns in diameter.

9. A taste masking composition which comprises a therapeutically effective amount of a spray dried spheroidal microcapsule core under about 150 microns in diameter and a matrix over the core wherein the taste masking composition comprises:
(A) a microcapsule core comprising in percentages by weight of the core composition:
  (a) sucralfate present in an amount from about 1% to about 70%; and
  (b) a polymer soluble in the gastric fluids present in an amount from about 30% to about 99%; and
(B) a matrix over the core comprising in percentages by weight of the matrix composition:
  (a) a bulking agent present in an amount up to about 99.9%; and
  (b) a lubricating agent present in an amount from about 0.1% to about 7%.

10. The composition according to claim 9, wherein sucralfate is present in an amount from about 1% to about 60%, by weight of the core composition.

11. The composition according to claim 9, wherein the polymer soluble in the gastric fluids is present in an amount from about 40% to about 99%, by weight of the core composition.

12. The composition according to claim 9, wherein the polymer soluble in the gastric fluids is selected from the group consisting of maltodextrins, gelatin, acacia, agar, alginic acid, carrageenan, guar, pectin, tragacanth, xanthan, carboxymethyl cellulose, methyl cellulose, microcrystalline cellulose, polyacrylic acid, polyvinyl alcohol, polyvinyl pyrrolidone polymers, and mixtures thereof.

13. The composition according to claim 9, wherein the polymer soluble in the gastric fluids is selected from the group consisting of maltodextrins, gelatin, alginic acid, and mixtures thereof.

14. The composition according to claim 9, wherein the bulking agent is present in an amount up to about 98%, by weight of the matrix composition.

15. The composition according to claim 9, wherein the bulking agent is selected from the group of sugar alcohols consisting of sorbitol, xylitol, mannitol, galactitol, maltitol, and mixtures thereof.

16. The composition according to claim 9, wherein the lubricating agent is present in an amount from about 0.5% to about 6%, by weight of the matrix composition.

17. The composition according to claim 9, wherein the lubricating agent is selected from the group consisting of magnesium stearate, calcium stearate, zinc stearate, stearic acid, talc, waxes, and mixtures thereof.

18. The composition according to claim 9, wherein the matrix further comprises a binding agent present in an amount from about 2% to about 15%, by weight of the matrix composition.

19. The composition according to claim 18, wherein the binding agent is selected from the group consisting of pregelatinized starch, sucrose, polyethylene glycol, and mixtures thereof.

20. The composition according to claim 9, wherein the weight ratio of microcapsule core composition to matrix composition is from about 1:9 to about 9:1, respectively.

21. A method for preparing spray dried spheroidal microcapsules under about 150 microns in diameter, which comprises the steps of:
(A) providing the following ingredients, in percentages by weight of the microcapsule composition:
  (a) sucralfate present in an amount from about 1% to about 70%; and
  (b) a polymer soluble in the gastric fluids present in an amount from about 30% to about 99%; and
(B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and
(C) feeding the mixture of step (B) into a spray dryer and spray drying the mixture under controlled conditions such that spheroidal microcapsules under about 150 microns in diameter are formed.

22. The method according to claim 21, wherein sucralfate is present in an amount from about 1% to about 60%, by weight of the microcapsule composition.

23. The method according to claim 21, wherein the polymer soluble in the gastric fluids is present in an amount from about 40% to about 99%, by weight of the microcapsule composition.

24. The method according to claim 21, wherein the polymer soluble in the gastric fluids is selected from the group consisting of maltodextrins, gelatin, acacia, agar, alginic acid, carrageenan, guar, pectin, tragacanth, xanthan, carboxymethyl cellulose, methyl cellulose, microcrystalline cellulose, polyacrylic acid, polyvinyl alcohol, polyvinyl pyrrolidone polymers, and mixtures thereof.

25. The microcapsule according to claim 24, wherein the polymer soluble in the gastric fluids is selected from the group consisting of maltodextrins, gelatin, alginic acid, and mixtures thereof.

26. The method according to claim 21, further comprising a plasticizing agent present in an amount from about 5% to about 30%, by weight of the microcapsule composition.

27. The microcapsule according to claim 26, wherein the plasticizing agent is selected from the group consisting of ethylene glycol, propylene glycol, acetyltributylcitrate, and mixtures thereof.

28. The method according to claim 21, wherein sucralfate in the aqueous mixture of step (B) is prepared in a concentration from about 1% to about 60%, by weight of the aqueous mixture.

29. The method according to claim 21, wherein the polymer soluble in the gastric fluids in the aqueous mixture of step (B) is prepared in a concentration from about 5% to about 60%, by weight of the aqueous mixture.

30. The method according to claim 21, wherein the controlled conditions in the spray drying step of step (C) include an air inlet temperature from about 60° C. to about 145° C.

31. The method according to claim 21, wherein the controlled conditions in the spray drying step of step (C) include an air outlet temperature from about 40° C. to about 90° C.

32. The method according to claim 21, wherein the spray dried spheroidal microcapsules in step (C) are under about 100 microns in diameter.

33. A method for preparing a taste masking composition which comprises a therapeutically effective amount of a spray dried spheroidal microcapsule core under about 150 microns in diameter and a matrix over the core which comprises the steps of:
  (A) providing the following ingredients of the microcapsule core in percentages by weight of the core composition:
    (a) sucralfate present in an amount from about 1% to about 70%; and
    (b) a polymer soluble in the gastric fluids present in an amount from about 30% to about 99%; and
  (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and
  (C) feeding the mixture of step (B) into a spray dryer and spray drying the mixture under controlled conditions such that spheroidal microcapsules under about 150 microns in diameter are formed;
  (D) providing the following ingredients of the matrix, in percentages by weight of the matrix composition:
    (a) a bulking agent present in an amount up to about 99.9%; and
    (b) a lubricating agent present in an amount from about 0.1% to about 7%; and
  (E) preparing a homogeneous mixture of the ingredients in step (D); and
  (F) preparing a homogeneous mixture of the spray dried microcapsules from step (C) and the matrix mixture from step (E) and compressing the homogeneous mixture into tablets.

34. The method according to claim 33, wherein sucralfate in the microcapsule core in step (A) is present in an amount from about 1% to about 60%, by weight of the core composition.

35. The method according to claim 33, wherein the polymer soluble in the gastric fluids in the microcapsule core in step (A) is present in an amount from about 5% to about 60%, by weight of the core composition.

36. The method according to claim 33, wherein the polymer soluble in the gastric fluids is selected from the group consisting of maltodextrins, gelatin, acacia, agar, alginic acid, carrageenan, guar, pectin, tragacanth, xanthan, carboxymethyl cellulose, methyl cellulose, microcrystalline cellulose, polyacrylic acid, polyvinyl alcohol, polyvinyl pyrrolidone polymers, and mixtures thereof.

37. The method according to claim 33, further comprising a plasticizing agent present in an amount from about 5% to about 30%, by weight of the microcapsule composition.

38. The method according to claim 33, wherein the bulking agent in the matrix in step (D) is present in an amount up to about 98%, by weight of the matrix composition.

39. The method according to claim 33, wherein the bulking agent is a sugar alcohol.

40. The method according to claim 33, wherein the lubricating agent is present in an amount from about 0.5% to about 6%, by weight of the matrix composition.

41. The method according to claim 33, wherein the matrix further comprises a binding agent present in an amount from about 2% to about 15%, by weight of the matrix composition.

42. The method according to claim 33, wherein the weight ratio of microcapsule core composition to matrix composition is from about 1:9 to about 9:1, respectively.

43. A spray dried spheroidal microcapsule under about 150 microns in diameter prepared by a method which comprises the steps of:
  (A) providing the following ingredients, in percentages by weight of the microcapsule composition:
    (a) sucralfate present in an amount from about 1% to about 70%; and
    (b) a polymer soluble in the gastric fluids present in an amount from about 30% to about 99%; and
  (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and
  (C) feeding the mixture of step (B) into a spray dryer and spray drying the mixture under controlled conditions such that spheroidal microcapsules under about 150 microns in diameter are formed.

44. A taste masking composition which comprises a therapeutically effective amount of a spray dried spheroidal microcapsule core under about 150 microns in diameter and a matrix over the core prepared by a method which comprises the steps of:
  (A) providing the following ingredients of the microcapsule core in percentages by weight of the core composition:
    (a) sucralfate present in an amount from about 1% to about 70%; and
    (b) a polymer soluble in the gastric fluids present in an amount from about 30% to about 99%; and
  (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and
  (C) feeding the mixture of step (B) into a spray dryer and spray drying the mixture under controlled conditions such that spheroidal microcapsules under about 150 microns in diameter are formed;
  (D) providing the following ingredients of the matrix, in percentages by weight of the matrix composition:
    (a) a bulking agent present in an amount up to about 99.9%; and
    (b) a lubricating agent present in an amount from about 0.1% to about 7%; and
  (E) preparing a homogeneous mixture of the ingredients in step (D); and
  (F) preparing a homogeneous mixture of the spray dried microcapsules from step (C) and the matrix mixture from step (E) and compressing the homogeneous mixture into tablets.

45. A taste masking composition which comprises a pharmaceutically acceptable carrier and a therapeutically effective amount of a spray dried spheroidal microcapsule core under about 150 microns in diameter wherein the microcapsule core composition comprises:
   (a) sucralfate present in an amount from about 1% to about 70%; and
   (b) a polymer soluble in the gastric fluids present in an amount from about 30% to about 99%.

46. The taste masking composition according to claim 45, wherein the pharmaceutically acceptable carrier is selected from the group consisting of a lozenge, a toffee, a nougat, a suspension, and a chewy candy.

47. A method for preparing a taste masking composition which comprises a pharmaceutically acceptable carrier and a therapeutically effective amount of a spray dried spheroidal microcapsule core under about 150 microns in diameter which comprises the steps of:
   (A) providing the following ingredients, in percentages by weight of the microcapsule composition:
      (a) sucralfate present in an amount from about 1% to about 70%; and
      (b) a polymer soluble in the gastric fluids present in an amount from about 30% to about 99%; and
   (B) preparing an aqueous homogeneous mixture of the ingredients in step (A), wherein sucralfate is present in a concentration from about 1% to about 60%, and the polymer soluble in the gastric fluids is present in a concentration from about 5% to about 60%, by weight of the aqueous mixture; and
   (C) feeding the mixture of step (B) into a spray dryer and spray drying the mixture under controlled conditions such that spheroidal microcapsules under about 150 microns in diameter are formed;
   (D) heating and mixing the pharmaceutically acceptable carrier in water at an elevated temperature;
   (E) cooling the pharmaceutically acceptable carrier to a temperature below about 120° C.;
   (F) preparing a homogeneous mixture of the spray dried microcapsules from step (C) and the pharmaceutically acceptable carrier from step (E); and
   (G) forming the resulting mixture into shapes.

* * * * *